United States Patent [19]

Collington et al.

[11] Patent Number: 4,482,549
[45] Date of Patent: Nov. 13, 1984

[54] AMINOCYCLOPENTANE ESTERS AND PHARMACEUTICAL FORMULATION

[75] Inventors: Eric W. Collington, Welwyn; Peter Hallett, Bassingbourn; Christopher J. Wallis, Royston; Norman F. Hayes, Hitchin; John Bradshaw, Ware; Malcolm Carter, Ware; Alan Wadsworth, Royston, all of England

[73] Assignee: Glaxo Group Limited, London, England

[21] Appl. No.: 578,014

[22] Filed: Feb. 8, 1984

Related U.S. Application Data

[63] Continuation of Ser. No. 510,969, Jul. 5, 1983, abandoned, which is a continuation of Ser. No. 418,976, Sep. 16, 1982, abandoned.

[30] Foreign Application Priority Data

Oct. 29, 1981 [GB] United Kingdom ............... 8132675
Apr. 29, 1982 [GB] United Kingdom ............... 8212489

[51] Int. Cl.$^3$ ................. A61K 31/55; A61K 31/535; C07D 295/14
[52] U.S. Cl. .................................. 424/244; 544/357; 544/360; 424/246; 544/364; 544/372; 424/248.5; 544/374; 544/379; 424/248.51; 544/396; 544/399; 424/248.54; 544/400; 546/187; 424/248.55; 546/191; 546/205; 424/250; 546/208; 546/213; 424/263; 546/214; 546/230; 424/267; 546/233; 546/234; 424/274; 546/235; 546/238; 544/58.1; 546/239; 546/281; 544/58.2; 548/517; 548/523; 544/58.5; 548/527; 548/567; 544/58.6; 548/568; 548/569; 544/58.7; 548/573; 260/239 BF; 544/82; 260/243.3; 260/244.4; 544/85; 260/245.7; 260/330.3; 544/87; 260/330.6; 260/330.9; 544/121; 544/130; 544/131; 544/141; 544/146; 544/152; 544/159; 544/158; 544/165; 544/162; 544/163; 544/167; 544/169; 544/171; 544/172

[58] Field of Search ............... 544/58.1, 58.2, 58.5, 544/58.6, 58.7, 82, 85, 87, 121, 130, 131, 141, 146, 152, 159, 158, 165, 163, 162, 169, 167, 171, 172, 357, 360, 364, 372, 374, 379, 396, 399, 400; 546/187, 191, 205, 208, 213, 214, 230, 233, 234, 235, 238, 239, 281; 548/523, 527, 517, 568, 567, 569, 573; 542/426; 260/239 BF, 243.3, 244.4, 245.7, 330.3, 330.6, 330.9; 424/244, 246, 248.5, 248.51, 248.54, 248.55, 250, 263, 267, 274

[56] References Cited

U.S. PATENT DOCUMENTS

| | | | |
|---|---|---|---|
| 4,182,903 | 1/1980 | Favara et al. | 562/503 |
| 4,189,606 | 2/1980 | Favara et al. | 562/455 |
| 4,239,778 | 12/1980 | Venton et al. | 424/305 |
| 4,265,891 | 5/1981 | Collington et al. | 424/244 |
| 4,327,092 | 4/1982 | Collington et al. | 424/246 |
| 4,342,756 | 8/1982 | Collington et al. | 424/244 |
| 4,371,530 | 2/1983 | Collington et al. | 424/244 |
| 4,409,213 | 10/1983 | Collington et al. | 424/244 |

FOREIGN PATENT DOCUMENTS 44711 7/1981 European Pat. Off. .

OTHER PUBLICATIONS

Le Breton, G. C. et al., Proc. Natl. Acad. Sci. USA 76: 4097, (1979).
Orth, D. et al., Topics in Current Chemistry, 72: 51–97, (1977).

Primary Examiner—Robert W. Ramsuer
Attorney, Agent, or Firm—Bernard, Rothwell & Brown

[57] ABSTRACT

Compounds are described of the formula

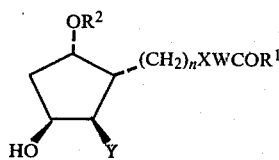

in which
—$COR^1$ is a complex ester or thioester group,
W is alkylene,
X is cis or trans —CH=CH or —$CH_2CH_2$—,
n is 1 or 2,
Y is a saturated heterocyclic amino group having 5–8 ring members, and
$R^2$ is unsubstituted or substituted phenylalkyl, thienzlalkyl, naphthylalkyl or cinnamyl, and their salts and solvates.

These compounds inhibit blood platelet aggregation and bronchoconstriction and may be formulated for use as antithrombotic and antiasthmatic agents.

9 Claims, No Drawings

AMINOCYCLOPENTANE ESTERS AND PHARMACEUTICAL FORMULATION

This is a continuation of application Ser. No. 510,969, filed July 5, 1983, abandoned which is a continuation of application Ser. No. 418,976, filed Sept. 16, 1982, now abandoned.

British Pat. Nos. 2,028,805, 2,070,591 and 2,075,503 referred to below correspond to Collington et al U.S. Pat. No. 4,265,891, application Ser. Nos. 223,315 and 223,314 (both filed on Jan. 8, 1981), U.S. Pat. No. 4,342,756 and U.S. Pat. No. 4,327,092, incorporated herein by reference.

The endoperoxides prostaglandins $G_2$ and $H_2$ and thromboxane $A_2$ are naturally occurring reactive metabolites of arachidonic acid in human platelets. They are not only potent aggregatory agents but are also constrictors of vascular and bronchial smooth muscle, and therefore substances which antagonise their effects are of considerable interest in human medicine.

We have now found a new group of compounds which have shown endoperoxide and thromboxane antagonist activity, and are therefore of interest in the treatment of asthma and cardiovascular diseases.

The invention thus provides compounds of the general formula (1)

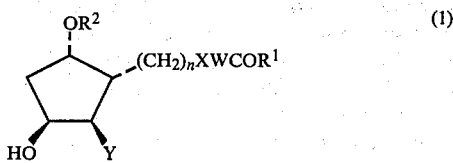

wherein $R^1$ is (a) $-AR^3$ where A is $-O-$ or $-S-$ and $R^3$ is phenyl [optionally substituted by $C_{1-4}$ alkyl (e.g. methyl, ethyl or t-butyl), $C_{1-4}$ alkoxy, (e.g. methoxy, ethoxy or butoxy), $C_{1-4}$ alkanoyl (e.g. acetyl), methylthio, methylsulphinyl, methylsulphonyl, halogen (e.g. chlorine or bromine),] $-CO_2R^4$ [where $R^4$ is a hydrogen atom or $C_{1-4}$ alkyl (e.g. methyl or ethyl) or phenyl], $-NHCOR^4$ (e.g. acetamido), $-CONR^5R^6$ [where $R^5$ and $R^6$ may be the same or different and are each a hydrogen atom or $C_{1-4}$ alkyl (e.g. methyl or ethyl)], $C_{1-4}$ alkylsulphonylamino [(e.g. $CH_3SO_2NH-$ or $C_2H_5SO_2NH-$), formyl, nitro, cyano, phenyl, or $-NR^5R^6$ (e.g. amino, dimethylamino or diethylamino];

(b) $-OCH_2COR^7$ where $R^7$ is phenyl [optionally substituted by a halogen atom (e.g. Cl or Br), $C_{1-4}$ alkyl (e.g. methyl, ethyl or t-butyl) or $C_{1-4}$ alkoxy, (e.g., methoxy, ethoxy or butoxy)] or $-NH_2$;

(c) $-A(CH_2)_mBR^5$ where m is 1-3 and B is $-O-$ or $-S-$, provided that when m is 1, $R^5$ is not a hydrogen atom (e.g. $CH_3OCH_2O-$, $CH_3CH_2OCH_2O-$, $CH_3SCH_2O-$ or $HOC_2H_4O-$);

(d) $-A(CH_2)_pR^8$ where p is 2 or 3 and $R^8$ is an N-attached $C_{1-4}$ dialkylamino (e.g. dimethyl- or diethylamino), morpholino, piperidino, pyrrolidino, acetylamino or benzoylamino group;

(e) $-OCH(CH_2N(CH_3)_2)_2$;

(f)

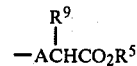

where $R^9$ is a hydrogen atom, methyl or phenyl; examples of suitable $R^5$ groups being methyl and ethyl;

(g) $-OCH_2OCOR^{10}$ where $R^{10}$ is $C_{1-4}$ alkyl (e.g. methyl or ethyl), methoxy or phenyl;

(h) $-OCH_2SCOR^{11}$ wherein $R^{11}$ is $C_{1-4}$ alkyl (e.g. methyl or ethyl);

(i) pyridinyloxy or pyridinylthio;

(j) 1-(acetyloxy)ethoxy, (acetyloxy)phenylmethoxy, tetrahydro-5-oxo-2-furanyloxy, tetrahydro-2-oxo-3-furanyloxy, triphenylmethoxy or diphenylmethoxy; or (k) $-OR^{12}$ where $R^{12}$ is $C_{3-6}$ alkenyl (e.g. propenyl or butenyl), $C_{5-7}$ cycloalkyl (e.g. cyclopentyl, cyclohexyl or cyclohepty) optionally substituted by one or more $C_{1-4}$ alkyl (e.g. methyl, ethyl or t-butyl) groups, $-CH_2CCl_3$ or furanylmethyl;

n is 1 or 2;

W is straight or branched $C_{1-7}$ alkylene;

X is cis or trans $-CH=CH-$ or $-CH_2CH_2-$;

Y is a saturated heterocyclic amino group (attached to the cyclopentane ring via the nitrogen atom) which has 5-8 ring members and (a) optionally contains in the ring $-O-$, $-S-$, $-SO_2-$, or $NR^{13}$ (where $R^{13}$ is a hydrogen atom, $C_{1-7}$ alkyl or aralkyl having a $C_{1-4}$ alkyl portion); and/or (b) is optionally substituted by one or more $C_{1-4}$ alkyl groups;

$R^2$ is (i) straight or branched $C_{1-5}$ alkyl substituted by (a) phenyl [optionally substituted by $C_{1-6}$ alkyl, $C_{5-7}$ cycloalkyl, phenylalkyl having a $C_{1-3}$ alkyl portion, thienyl, phenyl (optionally substituted by $C_{1-4}$ alkyl, $C_{1-4}$ alkoxy or phenyl), benzoyl (optionally substituted by $C_{1-4}$ alkyl, $C_{1-4}$ alkoxy, halogen, trifluoromethyl or phenyl) or $C_{5-7}$ cycloalkanoyl], (b) thienyl [optionally substituted by $C_{5-7}$ cycloalkyl or phenyl (optionally substituted by $C_{1-3}$ alkyl, $C_{1-3}$ alkoxy or halogen)], or (c) naphthyl (optionally substituted by $C_{1-4}$ alkyl or $C_{1-4}$ alkoxy), or (ii) cinnamyl (optionally substituted by benzoyl); and the physiologically acceptable salts and solvates thereof.

The structural formulae herein are to be understood to include the enantiomers of each of the compounds concerned as well as mixtures of the enantiomers including racemates, even though the precise structure as set out only relates to one enantiomer.

The amino group Y enables the compounds to form salts with organic acids, e.g. maleates. Also, when the group $R^1$ contains a $-COOH$ group, salts may be formed with bases. Examples of such salts are alkali metal (e.g. sodium), alkaline earth metal (e.g. calcium) and amine (e.g. piperazine) salts.

The heterocyclic amino group Y may for example have a 5,6 or 7-membered ring, e.g. pyrrolidino, piperidino, morpholino, piperazino, thiomorpholino, 1,1-dioxothiomorpholino, homomorpholino and hexamethyleneimino. Examples of the optional substituents which may be present on a second nitrogen atom in the ring are methyl, ethyl and benzyl. The carbon atoms of the heterocyclic rings may for example be substituted by methyl or ethyl. Y is preferably a morpholino or piperidino group.

In the group $-(CH_2)_nXWCOR^1$, n is preferably 2. X is preferably a cis $-CH=CH-$ group. The W group may for example contain 1-5 carbon atoms in a straight or branched chain and is preferably $-CH_2CH_2CH_2-$ when n is 1, and —CH$_2$CH$_2$— or —CH$_2$CH$_2$CH$_2$— when n is 2.

In the R$^1$ groups, A (where present) is preferably —O—. In R$^1$ groups of the type (a), R$^3$ is preferably phenyl (optionally substituted by C$_{1-4}$ alkyl C$_{1-4}$ alkoxy, C$_{1-4}$ alkanoyl, methylsulphonyl, —COOR$^4$ (where R$^4$ is a hydrogen atom or C$_{1-4}$ alkyl), —NHCOR$^4$ (where R$^4$ is C$_{1-4}$ alkyl) or —CONR$^5$R$^6$). In R$^1$ groups, of the type (b), R$^7$ is preferably —NH$_2$, phenyl or halophenyl. In R$^1$ groups of the type (c), m is preferably 1 or 2 and R$^5$ is preferably C$_{1-4}$ alkyl. In R$^1$ groups of the type (d), R$^8$ is preferably C$_{1-4}$ dialkylamino, morpholino or acetylamino. In R$^1$ groups of the type (f), R$^9$ is preferably methyl and R$^5$ is preferably C$_{1-4}$ alkyl.

Particularly preferred R$^1$ groups are —OCH$_2$OCOCH$_3$, —OCH$_2$SCH$_3$, —OCH$_2$CH$_2$CH$_2$NHCOCH$_3$, —OCH$_2$CONH$_2$, 4acetamidophenoxy and allyloxy.

When R$^2$ is a substituted alkyl group, the alkylene portion may for example contain 1–3 carbon atoms (e.g. methylene, ethylene or propylene) and is preferably a methylene group.

In R$^2$ groups of the type (i) (a), the phenyl group may be substituted by, for example, methyl, ethyl, t-butyl, cyclohexyl, benzyl, phenethyl, phenyl (optionally substituted by methyl, ethyl, methoxy or butoxy), benzoyl (optionally substituted by methyl, ethyl, methoxy, butoxy, chlorine or bromine) or cyclohexanoyl groups.

In R$^2$ groups of the type (i) (b), the thienyl group may be substituted by, for example, methyl, ethyl, methoxy, ethoxy, cyclohexyl or phenyl (optionally substituted by methyl, ethyl, methoxy, ethoxy, chlorine or bromine) groups.

R$^2$ is preferably a benzyl group in which the phenyl group is substituted by thienyl or phenyl (which phenyl group may itself be optionally substituted by C$_{1-4}$ alkyl or C$_{1-4}$ alkoxy).

Particularly preferred R$^2$ groups are benzyl groups in which the phenyl portion is substituted (preferably in the para-position) by a phenyl, tolyl or methoxyphenyl substituent.

A particularly preferred group of compounds has the formula (1) in which:

R$^1$ is —OCH$_2$OCOCH$_3$, —OCH$_2$SCH$_3$, —OCH$_2$CH$_2$CH$_2$NHCOCH$_3$, —OCH$_2$CONH$_2$, 4-acetamidophenoxy, or allyloxy, W is —CH$_2$CH$_2$— n is 2

X is cis —CH=CH—,

Y is piperidino and

R$^2$ is benzyl in which the phenyl group is substituted by phenyl, tolyl or methoxyphenyl and the physiologically acceptable salts and solvates thereof.

In general, the compounds of formula (1) in which the carbon atoms carrying the —(CH$_2$)$_n$XWCOR$^1$ group is in the R— configuration (and mixtures containing this isomer) are preferred.

Compounds of formula (1) inhibit blood platelet aggregation and bronchoconstriction. A test to determine inhibition of blood platelet aggregation is as described by G. V. Born in Nature 194, 927–929 (1962) except in that collagen is used instead of ADP as the proaggregatory agent. Alternatively, starved guineapigs are dosed orally with the compound to be tested in a suitable vehicle. Platelet rich plasma is prepared from each animal and aggregation to a range of collagen concentrations is measured after the method of Born (Nature 194, 927–929, (1962)). Collagen concentration-effect curves for each sample of plasma are calculated and results are expressed as the shift of the curves following treatment with the compound.

The ability of the compounds of the invention to inhibit bronchoconstriction is determined either in the anaesthetized guinea pig by measuring the effect of the compound to be tested on the dose response curve of the bronchoconstrictor [1R-[1α, 4α, 5β(Z), 6α-(1E, 3S*)]]-7-[6-(3-hydroxy-1-octenyl)-2-oxabicyclo[2,2,1-]hept-5-yl]-5-heptenoic acid (U-46619), or by the test described by K. M. Lulich et al in British Journal of Pharmacology 58, 71–79 (1976) except guinea pig lung is used instead of cat lung.

The compounds are thus of interest in the treatment of asthma, and as inhibitors of platelet aggregation and thrombosis for use in renal dialysis and the treatment and prevention of occlusive vascular diseases such as arteriosclerosis, atherosclerosis, peripheral vascular disease, cerebral vascular disease including transient ischaemic attacks, stroke, pulmonary embolism, diabetic retinopathy, post operative thrombosis, angina and myocardial infarction. They may be formulated in conventional manner for use, with one or more pharmaceutical carriers.

For oral administration, the pharmaceutical composition may take the form of, for example, tablets, capsules, powders, solutions, syrups, or suspensions prepared by conventional means with acceptable excipients.

The compounds may be formulated for parenteral administration by bolus injections or continuous infusion. Formulations for injections may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution before use with a suitable vehicle, e.g. sterile pyrogen-free water.

For administration by inhalation the compounds are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount.

For use as antithrombotic agents, the compounds are preferably administered orally, for example in amounts of 0.05 to 10 mg/kg body weight, 1 to 4 times daily.

For use in the treatment of asthma, the compounds may also be administered orally in amounts of 0.05 to 10 mg/kg body weight, 1 to 4 times daily; preferably however they are administered by inhalation at doses varying from 0.3 to 30 mg, 1 to 4 times daily. The compounds may be used in combination with other antiasthmatic agents.

The precise dose administered will of course depend on the age and condition of the patient.

Suitable methods for preparing the compounds of the invention are described below, the groups R$^1$, R$^2$, R$^3$, R$^5$, A, B, W, X and Y being as defined above except where otherwise indicated.

(a) The compounds of of the invention may be prepared by esterification of the corresponding carboxylic acid, i.e. a compound in which R$^1$ represents a hydroxyl group. Conventional esterification methods may be used.

For example, compounds in which $R^1$ is a group of the type a, c (other than those in which m is 1), d, e, f, and k may be prepared by treating a reactive derivative of the corresponding carboxylic acid with an appropriate alcohol or thiol $R^1H$. The reactions may for example be carried out at room temperature using a solvent such as a ketone (e.g. methylethyl ketone or acetone) or acetonitrile and, where appropriate, in the presence of pyridine.

The reactive derivative is conveniently a mixed anhydride of the acid, formed for example by treatment of the acid with a chloroformate in the presence of a suitable base, e.g. triethylamine or pyridine at $-10°$ C.

The chloroformate may for example be a $C_{1-6}$ alkyl (e.g. iso-butyl), aryl (e.g. phenyl) or aralkyl (e.g. benzyl) chloroformate.

The same group of esters may also be prepared by first reacting the corresponding carboxylic acid with dicyclohexylcarbodiimide in the presence of 4-pyrrolidinopyridine, and then treating the product with the alcohol or thiol $R^1H$. This reaction is conveniently performed at room temperature in a solvent such as ether or $CH_2Cl_2$.

Again for example, compounds in which $R^1$ is a group of the type b, c, d, f, g, h, or j and A (when present) is —O— may be prepared by reacting the corresponding carboxylic acid with an appropriate halide $R^{14}$Hal, where Hal represents halogen and $R^{14}$ is as just defined for $R^1$, excluding the terminal —O—. The reaction is carried out in the presence of a suitable base, e.g. potassium t-butoxide or potassium carbonate or a sterically hindered amine such as N,N-diisopropylethylamine, triethylamine or dicyclohexylamine in a suitable solvent (such as acetonitrile, dimethylformamide, $CH_2Cl_2$ or a ketone, e.g. methylethyl ketone or acetone), for example at a temperature from $0°$ C. to room temperature.

This latter reaction may also be used to prepare compounds in which $R^1$ is a group of type (c) in which A is —S— and m is 1, by reacting the corresponding thioacid (i.e. in which $R^1$ is —SH) with a halide $R^5BCH_2$—Hal. The thioacid starting material may be prepared in situ by treating a reactive derivative of the corresponding carboxylic acid (e.g. a mixed anhydride, as above) with a hydrosulphide (e.g. NaHS).

Compounds in which $R^1$ is a group of the type (f) where A is —O— may also be prepared by reacting the corresponding carboxylic acid with the appropriate diazoalkane in a solvent such as dioxan in the presence of a salt such as copper (II) chloride, for example at room temperature.

Compounds in which $R^1$ is a group of the type (i) where A is —S— may also be prepared by reacting the corresponding carboxylic acid with the appropriate pyridyldisulphide in the presence of triphenylphosphine in a solvent such as benzene, for example at room temperature.

Carboxylic acids required as starting materials for the preparation of compounds of formula (1) by process (a) may be prepared by selective reduction of the corresponding acid of formula (2) below using for example a selective reducing agent such as lithium tri-sec-butylborohydride in a solvent such as tetrahydrofuran at a temperature from $0°$ to $-78°$ C. Where a carbonyl group is present in $R^2$ this will need to be in a protected state during this reaction. Conventional protection methods may be used, with regard to the reducing conditions.

Many if the compounds of formula (2)

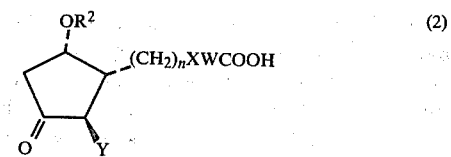

are described in British Patent Specification Nos. 2028805A, 2070591A and 2075503A and those containing other $R^2$ groups may be prepared by the same general methods, using starting materials containing the desired $R^2$ group.

(b) The compounds of the invention may also be prepared by reduction of a corresponding compound in which X is an acetylene group. Suitable methods of reduction include using hydrogen in the presence of a catalyst, e.g. palladium on a support (e.g. $CaCO_3$ or $BaSO_4$) and poisoned for example by lead or quinoline. Suitable solvents include ethyl acetate and methanol. This reaction is particularly suitable for preparing compounds in which X is cis —CH=CH—.

The acetylenes required as starting materials may be prepared by first brominating (e.g. with bromine in $CH_2Cl_2$) a compound of formula (3)

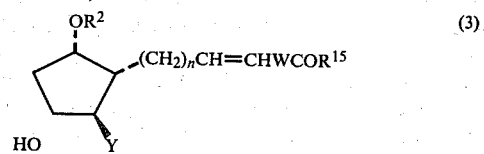

(where $R^{15}$ is $C_{1-6}$ alkoxy, e.g. methoxy) to give the corresponding compound in which X is —CHBr.CHBr—. The latter dibromo compound is then dehydrobrominated to form the acetylene group, for example in two stages, using potassium t-butoxide first at $0°$ C. and then at room temperature. Hydrolysis of the resulting acetylene ester to the corresponding acid ($R^1$=OH) using a base such as NaOH at e.g. room temperature, followed by oxidation of the ring hydroxy group (using e.g. chromic acid in acetone at a low temperature e.g. $-20°$ C. to room temperature) gives a corresponding acid in which X is an acetylene group and $R^1$ is —OH. Reduction of the product using e.g. lithium tri-sec-butylborohydride as described above for method (a) gives a corresponding compound of formula (1) in which X is an acetylene group and $R^1$ is —OH. Esterification of the acetylene acids as described in method (a) then gives the required acetylene ester starting materials. The starting materials of formula (3) may be prepared by the methods generally described in British Patent Specification Nos. 2028805A, 2070591A and 2075503A.

(c) Compounds in which $R^1$ is a group of type (a) in which $R^3$ is phenyl substituted by amino may be prepared by reduction of the corresponding compound in which $R^3$ is phenyl substituted by azido. The reduction may for example be effected with zinc and potassium dihydrogen phosphate in a suitable solvent, e.g. tetrahydrofuran.

(d) Compounds in which X is —$CH_1CH_2$— may be prepared by catalytic hydrogenation of a corresponding compound in which X is —CH=CH—, using a catalyst such as palladium oxide. Alcohols such as ethanol are suitable solvents and the reaction may be performed at room temperature.

(e) Where salts of compounds of formula (1) are desired such salts may be formed by conventional methods, for example by treatment with an acid or when $R^1$ contains a —COOH group, with a base. Salts of acids may be prepared by adding the acid to a solution of the compound of formula (1) in an organic solvent such as ether. Salts of bases may be prepared by adding the base (e.g. an amine such as piperazine) in a solvent such as ether.

When a specific enantiomer of formula (1) is required, starting materials having the desired stereochemical configuration should be used in the above processes. Such starting materials may for example be prepared from an enantiomeric bromohydrin as generally described in British Patent Specification No. 2075503A.

The following examples illustrate the invention.

'Jones reagent' is a solution of chromic acid and sulphuric acid in water. A 2.67M solution contains $CrO_3$ (26.7 g) and concentrated $H_2SO_4$ (23 ml) made up to 100 ml with water.

Temperatures are in °C. The following abbreviations are used: 'Dried' refers to drying with $MgSO_4$; T.L.C.—thin layer chromatography using $SiO_2$; PE—petroleum ether (boiling at 40°-60° unless otherwise stated); THF—tetrahydrofuran; DMF—dimethylformamide; ER—ether; EA—ethyl acetate; DMSO—dimethylsulphoxide; IPA—isopropyl alcohol. Chromatography was carried out using silica gel unless otherwise stated. The following abbreviations defined the eluent used for the chromatography and T.L.C.
(B) 9:1 ER-Methanol
(C) ER
(F) 9:1 EA-Methanol
(FF) 4:1 EA-Methanol
(GG) 24:1 ER-Methanol.
Further abbreviations for eluent used for chromatography.
(LL) 99:1 EA—$Et_3N$
(MM) 199:1 EA—$Et_3N$
(NN) 97:3 EA-methanol
(OO) 75:24:1 $CH_2Cl_2$—ER—$Et_3N$
(PP) 80:20:1 $CH_2Cl_2$—ER—$Et_3N$
(QQ) 66:34:1 $CH_2Cl_2$—ER—$Et_3N$
(RR) 95:5:0.5 EA—methanol—$Et_3N$
(SS) 4:1 PE-ER
(TT) 2:1 EA-methanol
(UU) 1:1 EA-PE (b.p. 60°-80°)
(VV) 50:50:1 $CH_2Cl_2$—ER—$Et_3N$
(WW) 90:10:1 EA-methanol-$Et_3N$
Additional abbreviation:
DIBAL—diisobutylaluminium hydride.

The preparation of Intermediate 1 is described in British Patent Specification No. 2075503A.

Intermediate 1

[1α(Z),2β,3β,5α]-(±)-7-[5-[[(1,1'-Biphenyl)-4-yl]methoxy]-3-hydroxy-2-(4-morpholinyl)cyclopentyl]-4-heptenoic acid The preparation of Intermediate 2 is described in British Patent Specification No. 2028805A.

Intermediate 2

[1α(Z),2β,5α]-(±)-7-[5-[[(1,1'-Biphenyl)-4-yl]methoxy]-2-(4-morpholinyl)-3-oxocyclopentyl]-5-heptenoic acid

Intermediate 3

[1α(Z),2β,3β,5α]-(±)-7-[5-[[(1,1'-Biphenyl)-4-yl]methoxy]-3-hydroxy-2-(4-morpholinyl)cyclopentyl]-5-heptenoic acid, compound with piperazine, (2:1)

A solution of Intermediate 2 (1 g) in THF (10 ml) was added dropwise to a stirred solution of lithium tri-sec-butylborohydride (1M in THF; 12 ml) under nitrogen at 0°-5°. After 2.25 h, the mixture was poured into $2N.H_2SO_4$ (30 ml) and pH 6.5 phosphate buffer (50 ml) and washed with ER. The aqueous layer was adjusted to pH 6.5 with 2N NaOH and extracted with EA (3×50 ml). The combined extracts were dried, evaporated and the residue purified by chromatography (FF) to give a foam (0.81 g). A portion of the foam (0.105 g) in ER (30 ml) was treated with piperazine (20.3 mg) in ER (1.8 ml) to give the title compound as a solid (0.11 g), m.p. 121°-127°.

The preparation of Intermediates 4 and 14 is described in British Patent Specification No. 2075503A.

Intermediate 4

[1R-(exo,endo)]-(−)-2-Bromo-3-hydroxybicyclo[3.2.0]heptan-6-one

Intermediate 5

[1R-endo,anti)]-(+)-5-Hydroxy-7-(1-piperidinyl)bicyclo[2.2.1]heptan-2-one

A solution of Intermediate 4 (5.25 g) in acetone (50 ml) containing piperidine (6.3 ml) was stirred at 20° for 2.5 h in the dark. The mixture was poured into 8% $NaHCO_3$ solution (150 ml) and extracted with $CH_2Cl_2$ (3×100 ml). The combined extracts were dried and evaporated and the residue was purified by chromatography (C). The title compound was obtained as a solid (4.7 g). A portion was recrystallised from ER-PE to give material of m.p. 87°-88°.

$[\alpha]_D^{25.5} = +68.7°$ ($CHCl_3$).

Intermediate 6

[1R-(endo,anti)]-(+)-5-[[(1,1'-Biphenyl)-4-yl]methoxy]-7-(1-piperidinyl)bicyclo[2.2.1]heptan-2-one A mixture of Intermediate 5 (4.34 g), benzyltriethylammonium chloride (2 g) and biphenylmethyl bromide (6.7 g) in $CH_2Cl_2$ (100 ml) and 17N NaOH (60 ml) was stirred vigorously at 20° for 18 h. The phases were separated and the aqueous phase, diluted with water (100 ml), was extracted with $CH_2Cl_2$ (3×100 ml). The combined organic layers were washed with water (100 ml), dried and evaporated and the residue was purified by chromatography (SS through to S). The title compound was obtained as a solid (6.2 g). A portion was recrystallised from EA-PE (b.p. 60°-80°) to give material of m.p. 108°-110°.

$[\alpha]_D^{22} = +25.45°$ ($CHCl_3$).

Intermediate 7

[1R-(endo,anti)]-(−)-6-[[(1,1'-Biphenyl)-4-yl]methoxy]-8-(1-piperidinyl)-2-oxabicyclo[3.2.1]octan-3-one Peracetic acid (13 ml; 6.12M) was added dropwise to stirred solution of Intermediate 6 (5.8 g) in $CH_2Cl_2$ (150 ml) at 20°. The mixture was stirred for 20 h, then diluted with water (250 ml). The phases were separated and the aqueous layer was extracted with $CH_2Cl_2$ (100 ml). The combined organic layers were added to a cold (0°) saturated solution of $Na_2SO_3$ (150 ml), then stirred vigorously at 20° for 1.5 h. The mixture was diluted with isopropyl acetate (200 ml) and the phases were separated. The aqueous layer was extracted with isopropyl acetate (2×100 ml) and the combined organic layers were washed with 0.5N NaOH (100 ml) and brine (150 ml), then dried and evaporated. The residue was purified by chromatography (EE) to give a solid which was recrystallised from ER-PE (b.p. 60°–80°) to give the title compound as a colourless solid (2.3 g), m.p. 129.5°–130°.

$[\alpha]_D^{22} = -26.5°$ (CHCl$_3$).

Intermediate 8

[1R-(1α,2β,3α,5α)]-5-[[(1,1'-Biphenyl)-4-yl]methoxy]-3-hydroxy-2-(1-piperidinyl)cyclopentane acetaldehyde A solution of Intermediate 7 (1.2 g) in dry $CH_2Cl_2$ (20 ml) was cooled (−78°) and stirred under nitrogen whilst a solution of DIBAL in hexane (5.25 ml; 1.43M) was added dropwise. Methanol (20 ml) was added dropwise at −70° after 0.75 h and the cooling bath was removed. After stirring at 20° for 1 h, the precipitate was filtered off and washed well with methanol. The combined filtrates were evaporated to give the title compound as a foam (1.2 g).

I.R. (CHBr$_3$) 3580, 3560, 2730, 1720 cm$^{-1}$.

Intermediate 9

[1R-(1α,2β,3α,4α)]-4-[[(1,1'-Biphenyl)-4-yl]methoxy]-3-(3-methoxy-2-propenyl)-2-(1-piperidinyl)cyclopentanol (Methoxymethyl)triphenylphosphonium chloride (3.8 g) was added over 10 min to a cold (−5°) stirred solution of potassium tert-butoxide (1.27 g) in dry THF (35 ml). After 30 min, a solution of Intermediate 8 (1.18 g) in THF (15 ml) was added at 0° and stirring maintained for 30 min. The mixture was poured into 8% NaHCO$_3$ solution (150 ml) and extracted with EA (2×100 ml). The combined extracts were dried and evaporated and the residue was purified by chromtography (FF) to give the title compound as a semi-solid (0.9 g).

I.R. (CHBr$_3$) 3580, 3500, 1650 cm$^{-1}$.

Intermediate 10

[2R-(2α,3β,4β)]-4-[[(1,1'-Biphenyl)-4-yl]methoxy]-3-(3-methoxy-2-propenyl)-2-(1-piperidinyl)cyclopentanone A solution of Intermediate 9 (0.84 g) in $CH_2Cl_2$ (8 ml) was cooled (5°) whilst triethylamine (1.95 ml) followed by pyridine-sulphur trioxide complex (1.27 g) in DMSO (8 ml) were added. After 1 h at 5° the mixture was poured into pH 6 phosphate buffer (100 ml) and extracted with ER (2×75 ml). The combined extracts were washed with water (50 ml) dried and evaporated and the residue was purified by chromatography (L) to give the title compound as an oil (0.725 g).

I.R. (CHBr$_3$) 1735, 1656 cm$^{-1}$.

Intermediate 11

[1R-(1α,2β,3β,5α)]-(+)-5-[[(1,1'-Biphenyl)-4-yl]methoxy]-3-hydroxy-2-(1-piperidinyl)cyclopentanepropanal A stirred solution of Intermediate 10 (0.69 g) in THF (15 ml) was cooled (−10°) whilst lithium tri-sec-butylborohydride in THF (5 ml; 1M) was added. After 1 h at −10°, 2N HCl (20 ml) was added, cautiously at first, and the mixture was stirred at 20° for 2 h. The mixture was washed with ER (50 ml) and then adjusted to pH 9 with 2N Na$_2$CO$_3$ and extracted with EA (4×50 ml). The combined extracts were dried and evaporated and the residue was purified by chromatography (TT) to give the title compound as a foam (0.206 g).

$[\alpha]_D^{23} = +54.90°$ (CHCl$_3$).

T.L.C. (TT) R$_f$ 0.13.

Intermediate 12

[1R-[1α(Z),2β,3β,5α]-(+)-Methyl 7-[5[[(1,1'-Biphenyl)-4-yl]methoxy]-3-hydroxy-2-(1-piperidinyl)cyclopentyl]-4-heptenoate To a stirred solution of potassium t-butoxide (2.05 g) in THF (80 ml) was added (3-carboxypropyl)triphenylphosphonium bromide (3.9 g). After 0.5 h at 20° a solution of Intermediate 11 (0.463 g) in THF (10 ml) was added and stirring continued at 20° for 0.75 h. Water (2 ml) was added and the solvent removed in vacuo. The residue was taken into water (100 ml), basified to pH 14 with 2N NaOH and washed with ER (3×60 ml). The aqueous solution was adjusted to pH 6.5 with 2N HCl and extracted with $CH_2Cl_2$ (3×50 ml). The combined extracts were concentrated, re-dissolved in 1:1 EA-$CH_2Cl_2$ (15 ml) and then treated with an excess of an ethereal solution of diazomethane. Excess diazomethane was destroyed with acetic acid and the solution then diluted with EA (30 ml) and washed with 2N Na$_2$CO$_3$ (40 ml). The organic solution was dried and evaporated and the residue purified by chromatography (FF) to give the title compound as an oil (0.428 g).

$[\alpha]_D^{23} = +60.10°$ (CHCl$_3$).

I.R. (Neat) 3600–3100(br.), 1735 cm$^{-1}$.

Intermediate 13

[1R-[1α(Z),2β,3β,5α]-(+)-7-[5-[[(1,1'-Biphenyl)-4-yl]methoxy]-3-hydroxy-2-(1-piperidinyl)cyclopentyl]-4-heptenoic acid, hydrochloride Intermediate 12 (10.38 g) was stirred with 74 OP ethanol (60 ml) and 5N NaOH (30 ml) at 20° for 16 h. The solution was diluted with water (400 ml) and then extracted with ER (2×150 ml). The aqueous phase was adjusted to pH 6 with 2N HCl and extracted with $CH_2Cl_2$ (3×200 ml). Evaporation of the combined extracts gave a foam (9.45 g), the majority (9.3 g) of which was taken up into $CH_2Cl_2$ (50 ml) and treated with an excess of an ethereal solution of hydrogen chloride. Evaporation in vacuo and trituration of the residue with Er (4×75 ml) gave the title compound as a powder (9.28 g). Crystallisation of a sample from EA-methanol gave material of m.p. 124°–126°.

$[\alpha]_D^{25} = +63.1°$ (CHCl$_3$).

Intermediate 14

(endo,anti)-(±)-5-Hydroxy-7-(1-piperidinyl)bicyclo[2.2.1]heptan-2-one, hydrochloride

Intermediate 15

(endo,anti)-(±)-5-[[4'-Methoxy(1,1'-biphenyl)-4-yl]methoxy]-7-(1-piperidinyl)bicyclo[2.2.1]heptan-2-one A mixture of Intermediate 14 (6.64 g), benzyltriethylammonium chloride (2 g) and 4-(bromomethyl)-4'-methoxy(1,1'-biphenyl) (9.73 g) in $CH_2Cl_2$ (100 ml) and 17N NaOH (70 ml) was vigorously stirred at 20° for 16 h. The mixture was poured into water (140 ml), the phases separated and the aqueous layer was extracted with $CH_2Cl_2$ (100 ml). The combined organic layers were dried and evaporated and the residue was triturated with PE (b.p. 60°–80°) (50 ml) to give a solid which was recrystallised from 5:2 EA-PE (b.p. 60°–80°) to give the title compound as a solid (6.63 g), m.p. 112°–115°.

Intermediate 16

(endo,anti)-(±)-6-[[4'-Methoxy(1,1'-biphenyl)-4-yl]methoxy]-8-(1-piperidinyl)-2-oxobicyclo[3.2.1]octan-3-one Peracetic acid (11.2 ml; 6.12M) was added slowly to a cooled (5°) stirred solution of Intermediate 15 (6.1 g) in $CH_2Cl_2$ (25 ml). The mixture was stirred at 20° for 64 h then added slowly to a cooled (5°) stirred mixture of saturated $Na_2SO_3$ (70 ml) and water (30 ml). After 1 h, isopropyl acetate (50 ml) was added and the layers were separated. The aqueous layer was extracted with isopropyl acetate (2×50 ml) and the combined organic layers were washed with 1N NaOH (100 ml) dried and evaporated. The residue was purified by chromtography (UU) to give an oil which was triturated with ER to give the title compound as a solid (2 g), m.p. 105°–106°.

Intermediate 17

(1α,2β,3α,5α)-(±)-3-Hydroxy-5-[[4'-methoxy(1,1'-biphenyl)-4-yl]methoxy]-2-(1-piperidinyl)cyclopentaneacetaldehyde DIBAL in hexane (7.9 ml; 1.43M) was added over 0.5 h to a cold (−70°), stirred solution of Intermediate 16 (1.9 g) in $CH_2Cl_2$ (15 ml). After 1.5 h methanol (15 ml) was added dropwise and the mixture was stirred at 20° for 2 h. The precipitate was filtered off and the solid was washed with methanol. The combined filtrates were evaporated and the residue was dissolved in $CH_2Cl_2$ (50 ml), dried and the solvent was removed to give the title compound as a foam (1.89 g).

I.R. ($CHBr_3$) 3580, 3535, 2730, 1710 cm$^{-1}$.

Intermediate 18

(1α,2β,3α,4α)-(±)-4-[[4'-Methoxy(1,1'-biphenyl)-4-yl]methoxy]-3-(3-methoxy-2-propenyl)-2-(1-piperidinyl) cyclopentanol (Methoxymethyl)triphenylphosphonium chloride (6.17 g) was added over 10 min to a cold (0°) solution of potassium tert-butoxide (2.02 g) in dry THF (35 ml). After 15 min, a solution of Intermediate 17 (1.86 g) in THF (10 ml) was added dropwise and stirring was maintained for 1.5 h. The mixture was poured into pH 6 phosphate buffer (100 ml) and extracted with EA (2×50 ml). The combined extracts were dried and evaporated and the residue was purified by chromatography (FF) to give the title compound as a semi-solid (1.29 g).

I.R. ($CHBr_3$) 3520, 3330, 1653 cm$^{-1}$.

Intermediate 19

(2α,3β,4β)-(±)-4-[[4'-Methoxy(1,1'-biphenyl)-4-yl]methoxy]-3-(3-methoxy-2-propenyl)-2-(1-piperidinyl) cyclopentanone A solution of Intermediate 18 (0.4 g) in $CH_2Cl_2$ (4 ml) was cooled (0°) whilst triethylamine (0.95 ml) followed by pyridine-sulphur trioxide complex (0.65 g) in DMSO (4 ml) were added. After 1 h at 0° the mixture was poured into pH 6.5 phosphate buffer (50 ml) and extracted with ER (2×50 ml). The combined extracts were washed with brine (2×25 ml) dried and evaporated and the residue was purified by chromatography (S) to give the title compound as an oil.

I.R. (Neat) 1740, 1655 cm$^{-1}$.

Intermediate 20

[1α,2β,3β,5α]-(±)-3-Hydroxy-5-[[4'-methoxy(1,1'-biphenyl)-4-yl]methoxy]-2-(1-piperidinyl)cyclopentanepropanal DIBAL (1.43M in hexane, 14 ml) was added over 10 min under nitrogen to an ice cooled solution of 2,6-di-t-butyl-p-cresol (8.8 g) in dry toluene (100 ml). After 1 h, the solution was cooled to −45° and a solution of Intermediate 19 (0.62 g) in toluene (20 ml) was added over 3 min. The temperature was allowed to rise to −10° over 1 h, then 2N HCl (40 ml) was added and the mixture stirred at room temperature for 1.5 h. The mixture was diluted with ER (100 ml) and the organic layer extracted with 1N $H_2SO_4$ (30 ml). The combined aqueous solutions were washed with ER (100 ml), basified with solid $NaHCO_3$ and the product extracted into $CH_2Cl_2$ (3×80 ml). The combined extracts were dried ($Na_2SO_4$) and concentrated, and the residue purified by chromatography (TT) to give the title compound as an oil (0.43 g).

I.R. (Neat) 3400(br.), 1720 cm$^{-1}$.

Intermediate 21

[1α(Z),2β,3β,5α-(±)-7-[3-Hydroxy-5-[[4'-methoxy(1,1'-biphenyl)-4-yl]methoxy]-2-(1-piperidinyl)cyclopentyl]-4-heptenoic acid, compound with ethyl acetate and dichloromethane (20:3:2)

(3-Carboxypropyl)triphenylphosphonium bromide (1.55 g) was added under nitrogen to a stirred solution of potassium t-butoxide (0.775 g) in dry THF (25 ml). After 40 min a solution of Intermediate 20 (0.43 g) in THF (7 ml) was added and the mixture stirred for 35 min at room temperature. Water (80 ml) followed by 2N NaOH (5 ml) were added and the mixture extracted with ER (2×100 ml). The aqueous solution was neutralised with 2N $H_2SO_4$, treated with pH 6.5 phosphate buffer (10%, 25 ml) and extracted with EA (2×70 ml). The combined extracts were washed with phosphate buffer (3×50 ml), dried ($Na_2SO_4$) and evaporated in vacuo to give the title compound as a foam (0.3 g).

I.R. ($CHBr_3$) 3200–2300(br.), 1720(br.) cm$^{-1}$.

Intermediate 22

[1R-[1α(Z),2β,3α,5α]-(+)-7-[5-[[(1-1'-Biphenyl)-4-yl]methoxy]-3-hydroxy-2-(1-piperidinyl)cyclopentyl]-5-heptenoic acid To a stirred solution of potassium-t-butoxide (5.9 g) in dry THF (70 ml) was added (4-carboxybutyl)triphenylphosphonium bromide(11.08 g) with stirring maintained at 20° under dry nitrogen for 0.5 h. A solution of Intermediate 8 (3.0 g) in dry THF (30 ml) was added and stirring continued at 20° for 50 min, whereupon water (15 ml) was added and excess solvent removed in vacuo. After dilution with water (20 ml) the solution was basified with 2N NaOH (30 ml) and extracted with ER (3×100 ml). The aqueous phase was adjusted to pH 7 with 2N HCl (35 ml) and extracted with $CH_2Cl_2$ (2×100 ml). The solution was then adjusted to pH 6 and extracted with $CH_2Cl_2$ (2×100 ml) and finally to pH 5.5 and extracted with $CH_2Cl_2$ (100 ml). The combined extracts were dried and evaporated to afford the crude title compound as a foam (3.71 g) which was purified via its methyl ester as described below.

To a stirred solution of the foam (0.496 g) in methanol (10 ml) at 20° was added concentrated $H_2SO_4$ (0.2 ml) and the mixture stirred for 2.75 h. The solution was then poured into 8% aqueous $NaHCO_3$ (20 ml) and extracted with $CH_2Cl_2$ (3×20 ml). The combined extracts were dried and evaporated, and the residue purified by chromatography (FF) to give an oil (0.438 g). To a solution of this oil (0.4 g) in methanol (2 ml) was added 5N NaOH (1.5 ml) and the mixture stirred at 20° for 2.3 h. After dilution with water (20 ml) the solution was extracted with ER (2×20 ml). The aqueous solution was adjusted to pH 6 with 2N HCl (2 ml) followed by pH 6 phosphate buffer solution (20 ml) and extracted with $CH_2Cl_2$ (3×20 ml). The combined extracts were dried and evaporated to afford the pure title compound as a foam (0.376 g).

I.R. ($CHBr_3$) 3500,1710(br), 1520 $cm^{-1}$.

$[\alpha]_D^{26} = +30.5°$ ($CHCl_3$)

Intermediate 23

[1R-[1α(Z),2β,5α]-Triphenylmethyl 7-5-[[(1,1'-Biphenyl)-4-yl]methoxy]-3-oxo-2-(1-piperidinyl)cyclopentyl]-5-heptenoate To a solution of Intermediate 22 (0.503 g) in $CH_2Cl_2$ (5 ml) at 4° was added trityl chloride (0.391 g) followed by triethylamine (0.22 ml) and the mixture stirred in an ice-bath for 0.5 h. More triethylamine (1.03 ml) was added followed by a solution of pyridine-sulphur trioxide complex (0.67 g) in dry DMSO (5 ml) and stirring maintained at 0°–10° for 3 h. The mixture was poured into pH 6 phosphate buffer solution (100 ml) then extracted with ER (100 ml, 2×50 ml). The combined extracts were washed with water (50 ml), dried and evaporated, and the residue purified by chromatography (L) to give the title compound as a foam (0.462 g).

I.R. ($CHBr_3$) 1740 $cm^{-1}$.

Intermediate 24

[1R-[1α(Z),2β,3β,5α]]-(+)-7-[5-[[(1,1'-Biphenyl)-4-yl]methoxy]-3-hydroxy-2-(1-piperidinyl)cyclopentyl]-5-heptenoic acid, compound with dicyclohexylamine (1:1)

DIBAL in hexane (1M, 32 ml) was added dropwise at 0° over 5 min to a solution of 2,6-di-t-butyl-4-methylphenol (13.47 g) in dry toluene (75 ml) under dry nitrogen and stirring maintained at 0° for 1 h. The solution was then cooled to −65° and a solution of Intermediate 23 (1.39 g) in dry toluene (25 ml) added dropwise. The mixture was stirred at −70° for 0.75 h, allowed to warm to −20° over 0.5 h and stored at that temperature for 14 h. After addition of 2N HCl (100 ml) the mixture was stirred at 20° for 2 h, then poured into water (100 ml) and ER (100 ml). The aqueous phase was separated, washed with ER (100 ml), then adjusted to pH 6 with 5N NaOH (35 ml) followed by pH 6 phosphate buffer solution (50 ml). This mixture was then extracted with $CH_2Cl_2$ (4×100 ml) and the combined extracts dried and concentrated to yield a foam (1.1 g). A portion (0.22 g) was dissolved in $CH_2Cl_2$ (2 ml) and treated with dicyclohexylamine (0.09 ml). After evaporation in vacuo the residue was triturated with solvent mixture (L) whereupon the title compound (0.23 g) crystallised, m.p. 101°–103°.

$[\alpha]_D^{24} = +27.3°$ ($CHCl_3$).

The preparation of Intermediate 25 is described in British Patent Specification No. 2075503A.

Intermediate 25

[1α(Z),2β,5α]-(±)-7-[5-[[4'-Methyl(1,1'-biphenyl)-4-yl]methoxy]-2-(4-morpholinyl)-3-oxocyclopentyl]-4-heptenoic acid

Intermediate 26

[1α(Z),2β,3β,5α]-(±)-7-[3-Hydroxy-5-[[4'-methyl(1,1'-biphenyl)-4-yl]methoxy]-2-(4-morpholinyl)cyclopentyl]-4-heptenoic acid A solution of Intermediate 25 (0.105 g) in dry THF (25 ml) was added over 5 min under nitrogen to a stirred solution of lithium tri-secbutylborohydride (1M in THF; 3 ml) at −30°. After 2 h the solution was allowed to rise to ambient temperature and then poured into 2N $H_2SO_4$ (15 ml) and extracted with ER (2×30 ml). The aqueous phase was adjusted to pH 6 and extracted with EA (3×30 ml). The combined extracts were washed with pH 6.5 phosphate buffer solution (15 ml), dried and concentrated. The residue was purified by chromatography (FF) to give the title compound as a foam (0.063 g).

I.R. ($CHBr_3$) 3500, 3400–2300, 1730, 1710 $cm^{-1}$.

EXAMPLE 1

[1α(Z), 2β,3β,5α]-(±)-(Methylthio)methyl 7-5-[[(1,1'-Biphenyl)-4-yl]methoxy]-3-hydroxy-2-(4-morpholinyl)cyclopentyl]-4-heptenoate Chloromethyl methyl sulphide (0.08 ml) was added to a stirred solution of Intermediate 1 (0.3 g) and dicyclohexylamine (0.14 ml) in dry DMF (3 ml) at room temperature. After 20 h the suspension was poured into saturated $NH_4Cl$ solution (30 ml) and extracted with EA (3×25 ml). The combined extracts were dried, filtered and evaporated to afford a mobile oil (0.3 g). Column chromatography using (C) as eluent gave the title compound as an oil (0.122 g).

TLC (C) $R_f$ 0.26.

Analysis Found: C, 68.7; H, 7.7; N, 2.6; $C_{31}H_{41}NO_5S$ requires: C, 69.0; H, 7.7; N, 2.6%.

EXAMPLE 2

[1α(Z), 2β,3β,5α]-(±)-(Acetyloxy)methyl 7-[5-[[(1,1'-Biphenyl)-4-yl]methoxy]-3-hydroxy-2-(4-morpholinyl)cyclopentyl]-4-heptenoate, compound with ethyl acetate (3:1)

To a solution of Intermediate 1 (0.431 g) in pure acetone (4 ml) at 20° was added triethylamine (0.31 ml) followed by bromomethyl acetate (0.305 g) in acetone (2 ml). The mixture was stirred at 20° for 2 h and then poured into pH 6 phosphate buffer (75 ml) and extracted with EA (2×40 ml). The combined extracts were dried, filtered and concentrated, and the residue purified by chromatography (B) to give the title compound as an oil (0.353 g).

TLC (F) $R_f$0.3. IR (Neat) 3440(br), 1760, 1120 cm$^{-1}$.

EXAMPLE 3

[1α(Z), 2β,3β,5α]-(±)-4-(Acetylamino)phenyl 7-[5-[[(1,1'-Biphenyl)-4-yl]methoxy]-3-hydroxy-2-(4-morpholinyl)cyclopentyl]-4-heptenoate, compound with ethyl acetate (5:1)

To a solution of Intermediate 1 (0.5 g) in pure acetone (10 ml) was added triethylamine (0.58 ml) and the mixture cooled to −10° (ice/EtOH). Isobutylchloroformate (0.41 ml) was added, followed after 0.5 h at −10° by 4-(acetylamino)phenol(0.474 g) in acetone (8 ml). After another 0.5 h at −10°, pyridine (1 ml) was added and the temperature allowed to rise to 20° over 2 h. The mixture was poured into 15% pH 6 phosphate buffer solution (100 ml) and extracted with EA (3×50 ml). The combined extracts were dried and evaporated, and the residue purified by chromatography (B) to give the title compound as a viscous gum (0.367 g).

TLC (FF) $R_f$0.43 IR (CHBr$_3$) 3420, 3380, 1750, 1685, 1505 cm$^{-1}$.

EXAMPLE 4

[1α(Z), 2β,3β,5α]-(±)-(Acetyloxy)methyl 7-[5-[[(1,1'-Biphenyl)-4-yl]methoxy]-3-hydroxy-2-(4-morpholinyl)cyclopentyl]-5-heptenoate A solution of the acid derived from Intermediate 3 (0.64 g) in acetone (10 ml) containing triethylamine (0.55 ml) and bromomethyl acetate (0.51 g) was stirred at 20° for 2.5 h then poured into pH 6.5 phosphate buffer (150 ml) and extracted with EA (3×50 ml). The combined extracts were dried and evaporated and the residue was purified by chromatography (GG) to give the title compound as an oil (0.47 g). I.R. (CHBr$_3$) 3500–3100, 1755 cm$^{-1}$.

Analysis Found: C,69.4; H, 7.5; N, 2.5; C$_{32}$H$_{41}$NO$_7$ Requires: C,69.7; H, 7.5; N, 2.5%.

EXAMPLE 5

[1R-[1α(Z), 2β,3β,5α]]-(+)-2-Propenyl 7-[5-[[(1,1'-Biphenyl)-4-yl]methoxy]-3-hydroxy-2-(1-piperidinyl)cyclopentyl]-4-heptenoate To a solution of Intermediate 13 (0.4 g) and diisopropylethylamine (0.68 ml) in DMF (5 ml) was added dropwise 3-bromopropene (0.27 ml). The mixture was stirred for 20 h then poured into pH 6 phosphate buffer (50 ml) and extracted with EA (3×50 ml). The combined extracts were dried and evaporated and the residue purified by chromatography (LL) to give the title compound (0.23 g) as an oil.

$[\alpha]_D^{25} = +61.9°$ (CHCl$_3$).

I.R. (Neat) 3400, 1730 cm$^{-1}$.

Analysis Found: C,76.3; H,8.7; N,2.8; C$_{33}$H$_{43}$NO$_4$ requires: C,76.6; H,8.4; N,2.7%.

EXAMPLE 6

[1R-[1α(Z),2β,3β,5α]]-(+)-Methoxymethyl 7-[5-[[(1,1'-Biphenyl)-4-yl]methoxy]-3-hydroxy-2-(1-piperidinyl)cyclopentyl]-4-heptenoate To a cold (0°) solution of Intermediate 13 (0.5 g) and diisopropylethylamine (0.42 ml) in DMF (6 ml) was added dropwise chloromethyl methyl ether (0.11 ml). The mixture was stirred for 3 h during which time ambient temperature was reached. The solution was poured into pH 6 phosphate buffer (50 ml) and extracted with EA (3×50 ml). The combined extracts were dried and evaporated and the residue purified by chromatography on alumina [initially (C) then (B)] to give the title compound (0.285 g) as an oil.

$[\alpha]_D^{23.5} = +60.3°$ (CHCl$_3$).

I.R. (Neat) 3400, 1745 cm$^{-1}$.

Analysis Found: C,73.5; H,8.5; N,2.95; C$_{32}$H$_{43}$NO$_5$ requires: C,73.7; H,8.3; N,2.7%.

EXAMPLE 7

[1R-[1α(Z),2β,3β,5α]]-(+)-(2-Oxo-2-phenylethyl) 7-[5-[[(1-1'-Biphenyl)-4-yl]methoxy]-3-hydroxy-2-(1-piperidinyl)cyclopentyl]-4-heptenoate, compound with ethyl acetate (2.5:1)

A solution of Intermediate 13 (0.4 g) in CH$_3$CN (12 ml) containing diisopropylethylamine (0.4 ml) was treated with α-bromoacetophenone (0.3 g) and stirred for 3 h. EA (100 ml) was added and the mixture washed with pH 6.5 phosphate buffer (2×40 ml) and brine (40 ml). The organic layer was dried and evaporated, and the residue purified by chromatography (MM) to give the title compound (0.4 g) as an oil.

$[\alpha]_D^{23.8} = +59.2°$ (CHCl$_3$).

I.R. (Neat) 1750, 1710 cm$^{-1}$.

Analysis Found: C,75.4; H,7.7; N,2.5; C$_{38}$H$_{45}$NO$_5$.0.4 C$_4$H$_8$O$_2$ requires: C,75.4; H,7.7; N,2.2%.

EXAMPLE 8

[1R-[1α(Z),2β,3β,5α]]-(+)-(2-Amino-2-oxoethyl) 7-[5-[[(1,1'-Biphenyl)-4-yl]methoxy]-3-hydroxy-2-(1-piperidinyl)cyclopentyl]-4-heptenoate, compound with ethyl acetate (2:1)

A solution of Intermediate 13 (0.5 g) in DMF (7.5 ml) containing diisopropylethylamine (0.5 ml) was treated with chloroacetamide (0.45 g) and sodium iodide (0.25 g) then stirred for 48 h. The mixture was poured into pH 6.5 phosphate buffer (80 ml) and extracted with EA (4×40 ml). The combined extracts were washed with brine, dried and evaporated, and the residue purified by chromatography [initially (MM) then (RR)] to give the title compound as an oil (0.242 g).

$[\alpha]_D^{25} = +57.4°$ (CHCl$_3$).

I.R. (CHBr$_3$) 3520, 3400, 1740, 1695 cm$^{-1}$.

Analysis Found: C,70.8; H,8.4; N,5.1; C$_{32}$H$_{42}$N$_2$O$_5$.0.5C$_4$H$_8$O$_2$ requires: C,70.6; H,8.0; N,4.8%.

EXAMPLE 9

[1R-[1α(Z),2β,3β,5α]]-(+)-(Methylthio)methyl 7-[5-[[(1,1'-Biphenyl)-4-yl]methoxy]-3-hydroxy-2-(1-piperidinyl)cyclopentyl]-4-heptenoate Chlormethylmethyl sulphide (0.15 ml) was added to a stirred mixture of Intermediate 13 (0.5 g), triethylamine (0.75 ml) and sodium iodide (ca. 5 mg) in dry DMF (7 ml). After 22 h further triethylamine (0.75 ml) and chloromethylmethyl sulphide (0.15 ml) were added and stirring continued for 18 h. The reaction mixture was diluted with pH 6.5 phosphate buffer (100 ml) and extracted with EA (2×50 ml). The combined extracts were washed with brine (40 ml), dried and evaporated, and the residue purified by chromatography [initially (PP) then (QQ)] to give the title compound (0.285 g) as an oil.

$[\alpha]_D^{24} = +57.8°$ (CHCl$_3$).
I.R. (Neat) 3400, 1740 cm$^{-1}$.
T.L.C. (LL) R$_f$ 0.28.

EXAMPLE 10

[1R-[1α(Z),2β,3β,5α]]-(+)-(Acetyloxy)methyl 7-[5-[[(1,1'-Biphenyl)-4-yl]methoxy]-3-hydroxy-2-(1-piperidinyl)-cyclopentyl]-4-heptenoate Bromomethyl acetate (0.25 ml) was added to an ice cooled, stirred mixture of Intermediate 13 (0.35 g) and triethylamine (0.8 ml) in acetone (8 ml). After 1 h the ice bath was removed and the mixture stirred at room temperature for 2.5 h. The mixture was diluted with pH 6.5 phosphate buffer (80 ml) and extracted with EA (2×50 ml). The organic extracts were washed with brine (50 ml), dried and evaporated, and the residue purified by chromatography (OO) to give the title compound (0.224 g) as an oil.

$[\alpha]_D^{26} = +59.6°$ (CHCl$_3$).
I.R. (Neat) 3400, 1760 cm$^{-1}$.
Analysis Found: C,71.8; H,7.9; N,2.4; C$_{33}$H$_{43}$NO$_6$ requires: C,72.1; H,7.9; N,2.55%

EXAMPLE 11

[1α(Z),2β,3β,5α]-(±)-(Acetyloxy)methyl 7-[3-Hydroxy-5-[[4'-methoxy(1,1'-biphenyl)-4-yl]methoxy]-2-(1-piperidinyl)cyclpentyl]-4-heptenoate Bromomethyl acetate (0.06 ml) was added to an ice cooled, stirred solution of Intermediate 21 (0.125 g) and triethylamine (0.1 ml) in acetone (3 ml). After 1 h at 0° and 0.5 h at room temperature, further triethylamine (0.1 ml) and bromomethyl acetate (0.03 ml) were added. After 1 h, the mixture was diluted with pH 6.5 phosphate buffer (30 ml) and extracted with EA (2×30 ml). The combined extracts were washed with brine (20 ml), dried and evaporated, and the residue purified by chromatography [initially (E) then (NN)] to give the title compound (0.05 g) as an oil.

I.R. (CHBr$_3$) 1755 cm$^{-1}$.
Analysis Found: C,70.5; H,7.9; N,2.6; C$_{34}$H$_{45}$NO$_7$ requires: C,70.3; H,8.0; N,2.4%

EXAMPLE 12

[1R-[1α(Z),2β,3β,5α]-(+)-(Acetyloxy)methyl 7-[5-[[(1,1'-Biphenyl)-4-yl]methoxy]-3-hydroxy-2-(1-piperidinyl)cyclopentyl]-5-heptenoate To a solution of Intermediate 24 (0.64 g) in acetone (13 ml) was added triethylamine (0.93 ml) followed by a solution of bromomethyl acetate (0.902 g) in acetone (6 ml) and the mixture stirred at 20° for 4 h, then stored at 0°–5° for 13.5 h. The solution was then poured into pH 6 phosphate buffer solution (100 ml) and extracted with CH$_2$Cl$_2$ (3×80 ml). The combined extracts were dried, evaporated in vacuo, and the residue purified by column chromatography (PP) to give the title compound as an oil (0.313 g).

I.R. (CHBr$_3$) 3500–2600, 2810, 2760, 1760 cm$^{-1}$.
T.L.C. (FF) R$_f$ 0.48.
$[\alpha]_D^{25} = +33.6°$ (CHCl$_3$).

EXAMPLE 13

[1R-[1α(Z),2β,3β,5α]]-[4-(Acetylamino)phenyl] 7-[5-[[(1,1'-Biphenyl)-4-yl]methoxy]-3-hydroxy-2-(1-piperidinyl)cyclopentyl]-4-heptenoate Isobutyl chloroformate (0.24 ml) was added under nitrogen to a stirred, cooled (bath temp. −10°) mixture of the Intermediate 13 (0.3 g) and triethylamine (0.47 ml) in pure acetone (7.5 ml). After 20 min, p-acetamidophenol (0.5 g) was added and the mixture stirred at −10° for 2.5 h and then at room temperature for 1 h.

The mixture was diluted with pH 6.5 phosphate buffer (80 ml) and extracted with EA (2×60 ml). The combined organic extracts were washed with brine (30 ml), dried and evaporated in vacuo to give a gum (0.76 g). The gum was redissolved in CH$_2$Cl$_2$ (20 ml), the solid filtered off and the filtrate evaporated in vacuo. The residue was purified by chromatography [initially (LL) then (VV)] to give the title compound as a foam (0.175 g).

I.R. (CHBr$_3$) 3425, 1750, 1690 cm$^{-1}$.
T.L.C. (WW, double elution) R$_f$ 0.34.

EXAMPLE 14

[1α(Z),2β,3β,5α] and [1α(E),2β,3β,5α]-(±)-(Methylthio)methyl 7-[3-Hydroxy-5-[[4'-methyl(1,1'-biphenyl)-4-yl]methoxy]-2-(4-morpholinyl)cyclopentyl]-4-heptenoate, from Intermediate 26 by the method of Example 1 Purification by chromatography (E) gave material of Z:E/2:1

I.R. (CHBr$_3$) 3500–3100, 1730 cm$^{-1}$.
m/e Found: 554.2955 (m+1).
C$_{32}$H$_{44}$NO$_5$S requires: 554.2940 (m+1).

PHARMACEUTICAL EXAMPLES

Tablets

These may be prepared by direct compression or wet granulation. The direct compression method is preferred but may not be suitable in all cases as it is dependent upon the dose level and physical characteristics of the active ingredient.

| A. Direct Compression | mg/tablet |
| --- | --- |
| Active ingredient | 100.00 |
| Microcrystalline Cellulose B.P.C. | 298.00 |
| Magnesium Stearate | 2.00 |
| Compression Weight | 400.00 mg |

The active ingredient is sieved through a 250 m$^{-6}$ sieve, blended with the excipients and compressed using 10.0 mm punches. Tablets of other strengths may be prepared by altering the compression weight and using punches to suit.

| B. Wet Granulation | mg/tablet |
| --- | --- |
| Active ingredient | 100.00 |
| Lactose B.P. | 238.00 |
| Starch B.P. | 40.00 |
| Pregelatinised Maize Starch B.P. | 20.00 |
| Magnesium Stearate B.P. | 2.00 |
| Compressed Weight | 400.00 mg |

The active ingredient is sieved through a 250 m$^{-6}$ sieve and blended with the lactose, starch and pregelatinised starch. The mixed powders are moistened with purified water, granules are made, dried, screened and blended with the magnesium stearate. The lubricated granules are compressed into tablets as described for the direct compression formulae. The tablets may be film coated with suitable film forming materials, e.g. methyl cellulose or hydroxylpropyl methyl cellulose using standard techniques. Alternatively the tablets may be sugar coated.

| Capsules | mg/capsule |
| --- | --- |
| Active ingredient | 100.00 |
| *STA-RX 1500 | 99.00 |
| Magnesium Stearate B.P. | 1.00 |
| Fill Weight | 200.00 mg |

*A form of directly compressible starch supplied by Colorcorn Ltd., Orpington, Kent.

The active ingredient is sieved through a 250 m$^{-6}$ sieve and blended with the other materials. The mix is filled into No. 2 hard gelatin capsules using a suitable filling machine. Other doses may be prepared by altering the fill weight and if necessary changing the capsule size to suit.

| Inhalation Cartridges | /cartridge |
| --- | --- |
| Active ingredient (micronised) | 3 mg |
| Lactose B.P. to | 25 mg |

The active ingredient is micronised so that the majority of the particles are between 1 m$^{-6}$ and 5 m$^{-6}$ in longest dimensions and none are greater than 10 m$^{-6}$. The active ingredient is then blended with the lactose and the mix is filled into No. 3 hard gelatin capsules using a suitable filling machine.

| Suspensions | mg/5 ml dose |
| --- | --- |
| Active ingredient | 100.0 |
| Aluminium monostearate | 75.0 |
| Sucrose (powdered) | 125.0 |
| Flavour | as required |
| Colour | |
| Fractionated coconut oil to | 5.00 ml. |

The aluminium monostearate is dispersed in about 90% of the fractionated coconut oil. The resulting suspension is heated to 115° C. while stirring and then cooled. The flavour and colour are added and the active ingredient and sucrose are suitably dispersed. The suspension is made up to volume with the remaining fractionated coconut oil and mixed.

| Injection for Intravenous Administration | |
| --- | --- |
| Active ingredient | 50 mg |
| Suitable vehicle to | 5 ml. |

A sterile presentation of the active ingredient in an ampoule or vial together with an ampoule containing a suitable vehicle. The former may be prepared by (a) filling sterile material into vials under aseptic conditions (b) freeze drying a sterile solution of the active ingredient under aseptic conditions.

The vehicle may be (a) Water for Injections B.P. (b) Water for Injections B.P. containing: (1) sodium chloride to adjust the tonicity of the solution and/or (2) buffer salts or dilute acid or alkali to facilitate solution of the active ingredient.

The vehicle is prepared, clarified and filled into appropriate sized ampoules sealed by fusion of the glass. The vehicle is sterilised by heating in an autoclave using one of the acceptable cycles.

We claim:

1. Compounds of the general formula (1)

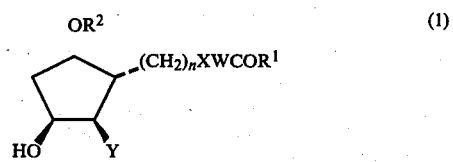

wherein R$^1$ is
(a) —AR$^3$ where A is —O— or —S— and R$^3$ is phenyl —CO$_2$R$^4$, —NHCOR$^4$, —CONR$^5$R$^6$
(b) —OCH$_2$COR$^7$ where R$^7$ is phenyl or —NH$_2$;
(c) —A(CH$_2$)$_m$BR$^5$ where m is 1-3 and B is —O— or —S—, provided that when m is 1, R$^5$ is not a hydrogen atom;
(d) —A(CH$_2$)$_p$R$^8$ where p is 2 or 3 and R$^8$ is an N-attached C$_{1-4}$ dialkylamino, morpholino, piperidino, pyrrolidino, acetylamino or benzoylamino group;
(e) —OCH(CH$_2$N(CH$_3$)$_2$)$_2$
(f)

where R$^9$ is a hydrogen atom, methyl or phenyl;
(g) —OCH$_2$OCOR$^{10}$ where R$^{10}$ is C$_{1-4}$ alkyl, methoxy or phenyl;
(h) —OCH$_2$SCOR$^{11}$ wherein R$^{11}$ is C$_{1-4}$ alkyl;
(i) pyridinyloxy or pyridinylthio;
(j) 1-(acetyloxy)ethoxy, (acetyloxy)phenylmethoxy, tetrahydro-5-oxo-2-furanyloxy, tetrahydro-2-oxo-3-furanyloxy, triphenylmethoxy or diphenylmethoxy; or
(k) —OR$^{12}$ where R$^{12}$ is C$_{3-6}$ alkenyl, C$_{5-7}$ cycloalkyl, —CH$_2$CCl$_3$ or furanylmethyl;
n is 1 or 2;
W is straight or branched C$_{1-7}$ alkylene;
X is cis or trans —CH=CH— or —CH$_2$CH$_2$—;
Y is a saturated heterocyclic amino group which has 5-8 ring members and (a) optionally contains in the ring —O—, —S—, —SO$_2$—, or NR$^{13}$; and (b) is optionally substituted by one or more $C_{1-4}$ alkyl groups;

$R^2$ is (i) straight or branched $C_{1-5}$ alkyl substituted by (a) phenyl, (b) thienyl, or (c) naphthyl, or (ii) cinnamyl;

and the physiologically acceptable salts and solvates thereof.

2. Compounds as claimed in claim 1 in which Y is morpholino or piperidino.

3. Compounds as claimed in claim 1 in which X is cis —CH=CH—.

4. Compounds as claimed in claim 1 in which n is 2 and W is —CH$_2$CH$_2$— or CH$_2$CH$_2$CH$_2$CH$_2$—.

5. Compounds as claimed in claim 1 in which $R^2$ is a benzyl group in which the phenyl group is substituted by thienyl or phenyl, which latter phenyl is optionally substituted by $C_{1-4}$ alkyl or $C_{1-4}$ alkoxy.

6. Compounds as claimed in claim 1 in which $R^1$ is —OCH$_2$OCOCH$_3$, —OCH$_2$SCH$_3$, —O(CH$_2$)$_3$NHCOCH$_3$, —OCH$_2$CONH$_2$, 4-acetamidophenoxy or allyloxy.

7. Compounds as claimed in claim 1 in which:
$R^1$ is —OCH$_2$OCOCH$_3$, —OCH$_2$SCH$_3$, —O(CH$_2$)$_3$NHCOCH$_3$, —OCH$_2$CONH$_2$, 4-acetamidophenoxy or allyloxy
W is —CH$_2$CH$_2$—,
n is 2,
X is cis —CH=CH—
Y is piperidino and
$R^2$ is benzyl in which the phenyl group is substituted by phenyl, tolyl or methoxyphenyl,
and the physiologically acceptable salts and solvates thereof.

8. Compounds as claimed in claim 1 in which the carbon atom carrying the —(CH$_2$)$_n$XWCOR$^1$ group is in the R— configuration.

9. A pharmaceutical composition comprising a compound as claimed in claim 1 and one or more pharmaceutical carriers.

* * * * *

UNITED STATES PATENT AND TRADEMARK OFFICE
CERTIFICATE OF CORRECTION

PATENT NO. : 4,482,549

DATED : November 13, 1984

INVENTOR(S) : Eric W. Collington et al.

It is certified that error appears in the above-identified patent and that said Letters Patent is hereby corrected as shown below:

Column 3, line 17, "4acetamidophenoxy" should read -- 4-acetamidophenoxy --.

Column 6, lines 30-38, the formula should read:

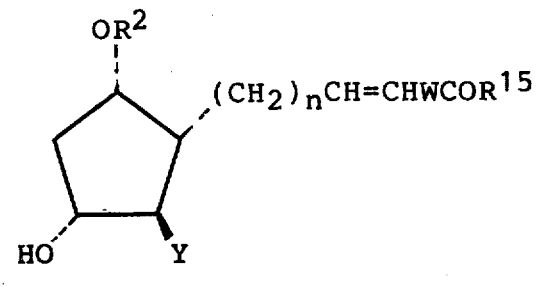

Column 8, line 33, "[1R-endo,anti)]-(+)-5-Hydroxy-7-(1-piperidinyl)bicy-" should read
-- [1R-(endo,anti)-(+)-5-Hydroxy-7-(1-piperidinyl)bicy- --.

UNITED STATES PATENT AND TRADEMARK OFFICE
CERTIFICATE OF CORRECTION

PATENT NO. : 4,482,549
DATED : November 13, 1984
INVENTOR(S) : Eric W. Collington et al.

It is certified that error appears in the above-identified patent and that said Letters Patent is hereby corrected as shown below:

Claim 1 should read as follows:

1. Compounds of the general formula (1)

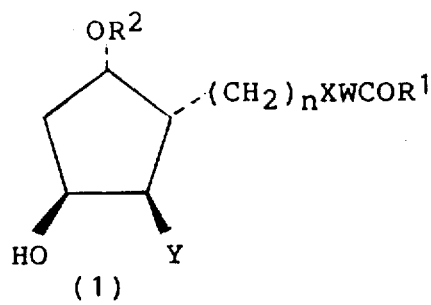

wherein $R^1$ is (a) $-AR^3$ where A is $-O-$ or $-S-$ and $R^3$ is phenyl [optionally substituted by $C_{1-4}$ alkyl, $C_{1-4}$ alkoxy, $C_{1-4}$ alkanoyl, methylthio, methylsulphinyl, methylsulphonyl, halogen, $-CO_2R^4$ (where $R^4$ is a hydrogen atom, $C_{1-4}$ alkyl or phenyl),

UNITED STATES PATENT AND TRADEMARK OFFICE
CERTIFICATE OF CORRECTION

PATENT NO. : 4,482,549

DATED : November 13, 1984

INVENTOR(S) : Eric W. Collington et al.

It is certified that error appears in the above-identified patent and that said Letters Patent is hereby corrected as shown below:

$-NHCOR^4$, $-CONR^5R^6$ (where $R^5$ and $R^6$ may be the same or different and are each a hydrogen atom or $C_{1-4}$ alkyl), $C_{1-4}$ alkylsulphonylamino, formyl, nitro, cyano, phenyl or $-NR^5R^6$];

(b) $-OCH_2COR^7$ where $R^7$ is phenyl (optionally substituted by a halogen atom, $C_{1-4}$ alkyl or $C_{1-4}$ alkoxy) or $-NH_2$;

(c) $-A(CH_2)_mBR^5$ where m is 1-3 and B is $-O-$ or $-S-$, provided that when m is 1, $R^5$ is not a hydrogen atom;

(d) $-A(CH_2)_pR^8$ where p is 2 or 3 and $R^8$ is an N-attached $C_{1-4}$ dialkylamino, morpholino, piperidino, pyrrolidino, acetylamino or benzoylamino group;

(e) $-OCH(CH_2N(CH_3)_2)_2$

UNITED STATES PATENT AND TRADEMARK OFFICE
CERTIFICATE OF CORRECTION

PATENT NO. : 4,482,549

DATED : November 13, 1984

INVENTOR(S) : Eric W. Collington et al.

It is certified that error appears in the above-identified patent and that said Letters Patent is hereby corrected as shown below:

(f)  $-A\overset{\overset{R^9}{|}}{C}HCO_2R^5$ where $R^9$ is a hydrogen atom, methyl or phenyl;

(g)  $-OCH_2OCOR^{10}$ where $R^{10}$ is $C_{1-4}$ alkyl, methoxy or phenyl;

(h)  $-OCH_2SCOR^{11}$ wherein $R^{11}$ is $C_{1-4}$ alkyl;

(i)  pyridinyloxy or pyridinylthio;

(j)  1-(acetyloxy)ethoxy, (acetyloxy)phenylmethoxy, tetrahydro-5-oxo-2-furanyloxy, tetrahydro-2-oxo-3-furanyloxy, triphenylmethoxy or diphenylmethoxy; or (k)  $-OR^{12}$ where $R^{12}$ is $C_{3-6}$ alkenyl, $C_{5-7}$ cycloalkyl (optionally substituted by one or more $C_{1-4}$ alkyl groups), $-CH_2CCl_3$ or furanylmethyl;

UNITED STATES PATENT AND TRADEMARK OFFICE
CERTIFICATE OF CORRECTION

PATENT NO. : 4,482,549
DATED : November 13, 1984
INVENTOR(S) : Eric W. Collington et al.

It is certified that error appears in the above-identified patent and that said Letters Patent is hereby corrected as shown below:

n is 1 or 2;

W is straight or branched $C_{1-7}$ alkylene;

X is cis or trans -CH=CH- or -CH$_2$CH$_2$-;

Y is a saturated heterocyclic amino group (attached to the cyclopentane ring via the nitrogen atom) which has 5 - 8 ring members and (a) optionally contains in the ring -O-, -S-, -SO$_2$-, or NR$^{13}$ (where R$^{13}$ is a hydrogen atom, $C_{1-7}$ alkyl or aralkyl having a $C_{1-4}$ alkyl portion); and (b) is optionally substituted by one or more $C_{1-4}$ alkyl groups;

R$^2$ is (i) straight or branched $C_{1-5}$ alkyl substituted by (a) phenyl [optionally substituted by $C_{1-6}$ alkyl, $C_{5-7}$ cycloalkyl, phenylalkyl having a $C_{1-3}$ alkyl portion, thienyl, phenyl (optionally substituted by $C_{1-4}$ alkyl, $C_{1-4}$ alkoxy or phenyl), benzoyl (optionally substituted by $C_{1-4}$

UNITED STATES PATENT AND TRADEMARK OFFICE
CERTIFICATE OF CORRECTION

PATENT NO. : 4,482,549

DATED : November 13, 1984

INVENTOR(S) : Eric W. Collington et al.

It is certified that error appears in the above-identified patent and that said Letters Patent is hereby corrected as shown below:

alkyl, $C_{1-4}$ alkoxy, halogen, trifluoromethyl or phenyl) or $C_{5-7}$ cycloalkanoyl], (b) thienyl [optionally substituted by $C_{5-7}$ cycloalkyl or phenyl (optionally substituted by $C_{1-3}$ alkyl, $C_{1-3}$ alkoxy or halogen)], or (c) naphthyl (optionally substituted by $C_{1-4}$ alkyl or $C_{1-4}$ alkoxy), or (ii) cinnamyl (optionally substituted by benzoyl);

and the physiologically acceptable salts and solvates thereof.

Signed and Sealed this

Twenty-fourth Day of September 1985

[SEAL]

Attest:

*Attesting Officer*

DONALD J. QUIGG

*Commissioner of Patents and Trademarks—Designate*